United States Patent [19]
Henry et al.

[11] Patent Number: 5,766,252
[45] Date of Patent: Jun. 16, 1998

[54] INTERBODY SPINAL PROSTHETIC IMPLANT AND METHOD

[75] Inventors: Patrick Henry, Levallois-Perret; Levon Doursounian, Paris, both of France

[73] Assignee: Osteonics Corp., Allendale, N.J.

[21] Appl. No.: 379,316

[22] Filed: Jan. 24, 1995

[51] Int. Cl.⁶ ..................................................... A61F 2/44
[52] U.S. Cl. ................................................. 623/17; 606/61
[58] Field of Search .............................. 623/16, 17, 18; 606/60, 61

[56] References Cited

U.S. PATENT DOCUMENTS 5,458,638   10/1995   Kuslich et al.

*Primary Examiner*—John G. Weiss
*Assistant Examiner*—Francis K. Cuddihy
*Attorney, Agent, or Firm*—Arthur Jacob

[57] ABSTRACT

An interbody spinal prosthetic implant is placed between adjacent vertebral bodies of the vertebrae of a spine to maintain a desired orientation and spacing between the adjacent vertebral bodies and support the adjacent vertebral bodies for fusion at the desired orientation and spacing, the prosthetic implant including a rigid member of biocompatible material having vertically opposite upper and lower load-bearing surfaces spaced apart a distance providing a height corresponding to the desired spacing, the rigid member having a wedge-shaped configuration in horizontal planes, the wedge-shaped configuration tapering from relatively narrower widths adjacent the front end toward relatively wider widths adjacent the rear end of the rigid body and providing the rigid body with an overall width wider than the height of the rigid body, and an ogival tip at the front end of the rigid member.

20 Claims, 5 Drawing Sheets

INTERBODY SPINAL PROSTHETIC IMPLANT AND METHOD

The present invention relates generally to prosthetic implants and pertains, more specifically, to an interbody spinal prosthetic implant for placement between adjacent vertebral bodies of the vertebrae of a spine and seating upon confronting end plates of the adjacent vertebral bodies to maintain a desired orientation and spacing between the adjacent vertebral bodies and support the adjacent vertebral bodies for fusion at the desired orientation and spacing, and to an improvement in the method of placement of the prosthetic implant.

Spinal prosthetic implants have been successful in the treatment of patients with ruptured, herniated, or otherwise degenerated intervertebral discs, or indications of spondylothesis. In such procedures, the spacing between adjacent vertebral bodies is restored by the insertion of prosthetic implants between the vertebral bodies and allowing interbody vertebral fusion to take place by bone ingrowth. While many of the spinal implant prostheses made available for these procedures require cutting into the bone of the vertebral bodies in order to secure the implants in place, some proposals for spinal prosthetic implants suggest that less invasive techniques can be utilized to achieve the desired result without the necessity for cutting into the bone itself.

The present invention provides a spinal prosthetic implant and technique which enable restoration of the desired intervertebral spacing and orientation between adjacent vertebral bodies and promotes fusion at the site, without the necessity for highly invasive surgical procedures. As such, the present invention attains several objects and advantages, some of which are summarized as follows: Restores intervertebral spacing and orientation between adjacent vertebral bodies, in the treatment of ruptured, herniated, or otherwise degenerated intervertebral discs, or indications of spondylothesis, and enables fusion between the adjacent vertebral bodies, with less invasive surgical procedures; provides a construction and configuration which facilitates appropriate introduction and placement of the prosthesis during implant, while reducing the risk of injury to surrounding tissue and organs; enables improved load distribution for reducing the risk of impaction of the bone of the surrounding vertebral bodies between which the prosthesis is placed; provides for relatively high strength support between adjacent vertebral bodies during fusion while placing graft material in position for maximum contact between the graft material and the adjacent vertebral bodies so as to promote and accelerate fusion; facilitates visualization of the placement of the prosthetic implant through the use of conventional radiological and magnetic resonance imaging (MRI) techniques; enables relatively economical manufacture with consistent high quality.

The above objects and advantages, as well as further objects and advantages, are attained by the present invention which may be described briefly as an interbody spinal prosthetic implant for placement between adjacent vertebral bodies of the vertebrae of a spine and seating upon confronting end plates of the adjacent vertebral bodies to maintain a desired orientation and spacing between the adjacent vertebral bodies and support the adjacent vertebral bodies for fusion at the desired orientation and spacing, the prosthetic implant comprising: a rigid member of biocompatible material having vertically opposite upper and lower load-bearing surfaces spaced apart altitudinally to define a height and located along mean planes extending in generally horizontal directions corresponding to the desired orientation and spaced apart a distance corresponding to the desired spacing, the rigid member including, a front end, a rear end spaced longitudinally from the front end to define a length, and sides spaced apart laterally to define a width and extending generally longitudinally at an angle to one another along a wedge-shaped configuration in the rigid member in horizontal planes, the wedge-shaped configuration tapering from narrower widths adjacent the front end toward wider widths adjacent the rear end and including an overall width greater than the height between the upper and lower load-bearing surfaces; and a tip extending longitudinally between the front end and the load-bearing surfaces, the tip having a surface contour tapered from transverse cross-sectional profiles of relatively lesser height and relatively narrower width adjacent the front end toward transverse cross-sectional profiles of relatively greater height and relatively wider width adjacent the load-bearing surfaces. Further, the present invention includes an improvement in a method for treatment of a spine having a degenerated intervertebral disc between adjacent vertebral bodies of the vertebrae of the spine by the placement of an interbody spinal prosthetic implant at a desired location between the adjacent vertebral bodies, at which desired location the prosthetic implant is seated upon confronting end plates of the adjacent vertebral bodies to maintain a desired orientation and spacing between the adjacent vertebral bodies and support the adjacent vertebral bodies for fusion at the desired orientation and spacing, the improvement comprising: establishing a bore in the disc, the bore having a diameter matching the desired spacing between the adjacent vertebral bodies; inserting the prosthetic implant into the bore, the prosthetic implant including a rigid member of biocompatible material having vertically opposite upper and lower load-bearing surfaces spaced apart altitudinally to define a height and located along mean planes extending in generally horizontal directions corresponding to the desired orientation and spaced apart a distance corresponding to the desired spacing, the rigid member including a front end, a rear end spaced longitudinally from the front end to define a length, sides spaced apart laterally to define a width and extending generally longitudinally at an angle to one another along a wedge-shaped configuration in the rigid member in horizontal planes, the wedge-shaped configuration tapering from narrower widths adjacent the front end toward wider widths adjacent the rear end, and a tip extending longitudinally between the front end and the load-bearing surfaces, the tip having a surface contour tapered from transverse cross-sectional profiles of lesser height and narrower width adjacent the front end toward transverse cross-sectional profiles of greater height and wider width adjacent the load-bearing surfaces; and advancing the prosthetic implant in the bore until the prosthetic implant is wedged into the tissue of the disc and is secured in place in the desired location between the adjacent vertebral bodies.

The invention will be understood more fully, while still further objects and advantages will become apparent, in the following detailed description of preferred embodiments of the invention illustrated in the accompanying drawing, in which.

Figure 1:
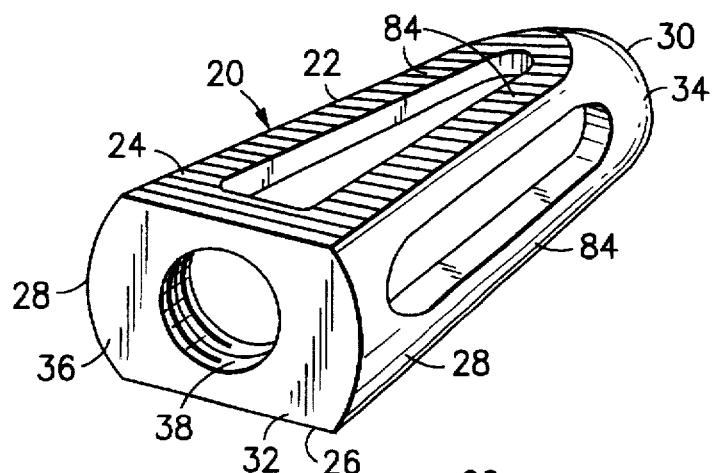
FIG. 1 is a rear perspective view of a prosthetic implant constructed in accordance with the invention.

Referring now to the drawing, and especially to FIG. 1 thereof, an interbody spinal prosthetic implant constructed in accordance with the present invention is shown at 20 and is seen to include a rigid member 22 of biocompatible material having vertically opposite load-bearing surfaces in the form of superior or upper surface 24 and inferior or lower surface 26. Sides 28 are spaced apart laterally and extend longitudinally along the rigid member 22 between an anterior or front end 30 and a posterior or rear end 32. An anterior or front tip 34 extends between the front end 30 and the upper and lower surfaces 24 and 26, and a posterior or rear wall 36 is located at the rear end 32. A threaded hole 38 is located in the rear wall 36 and extends longitudinally from the rear end 32 toward the front end 30, for purposes which will be set forth in detail below.

Turning now to FIGS. 2 through 6, the rigid member 22 of the prosthetic implant 20 extends longitudinally along a central axis C, has an overall longitudinal length L between the front end 30 and the rear end 32, and an overall width W between the sides 28. The upper and lower surfaces 24 and 26 each include laterally oriented serrations 40 which extend altitudinally with respect to a mean plane MP along which each of the upper and lower surfaces 24 and 26 are located. The mean planes MP extend in generally horizontal directions and are spaced apart altitudinally to define an overall height H. In the embodiment shown in FIGS. 2 through 6, the mean planes MP are parallel to one another so that the height H is essentially constant along the length of the upper and lower surfaces 24 and 26.

Figure 2:
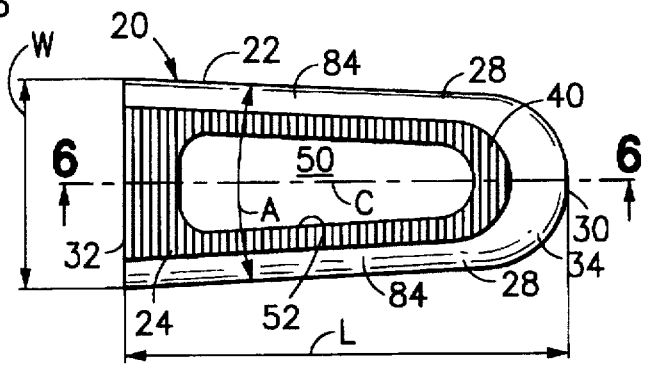
FIG. 2 is a top plan view of the prosthetic implant.
Figure 4:
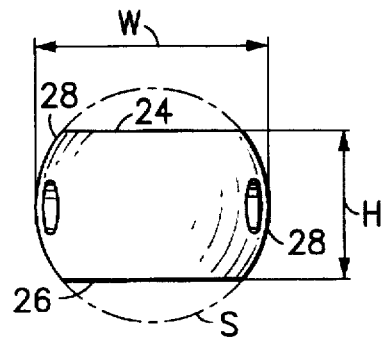
FIG. 4 is a front end view of the prosthetic implant.
Figure 5:
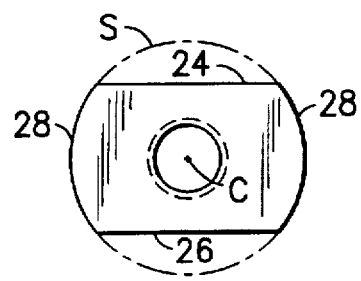
FIG. 5 is a rear end view of the prosthetic implant.

As best seen in FIG. 2, the sides 28 extend generally longitudinally at an angle A to one another and the rigid member 22 has a wedge-shaped configuration, in horizontal planes, the wedge-shaped configuration tapering from narrower widths adjacent the front end 30 to wider widths adjacent the rear end 32. In FIGS. 4 and 5, sides 28 each are seen to have a convex arcuate surface contour configuration, in lateral planes, the convex arcuate surface contour configuration extending altitudinally between the upper and lower surfaces 24 and 26 and lying on a circle S centered on the central axis C of the prosthetic implant 20 and having a diameter greater than the height H, so that the width W is greater than the height H.

Figure 3:
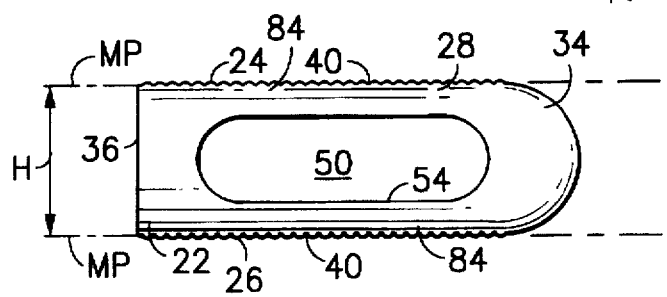
FIG. 3 is a side elevational view of the prosthetic implant.
Figure 6:
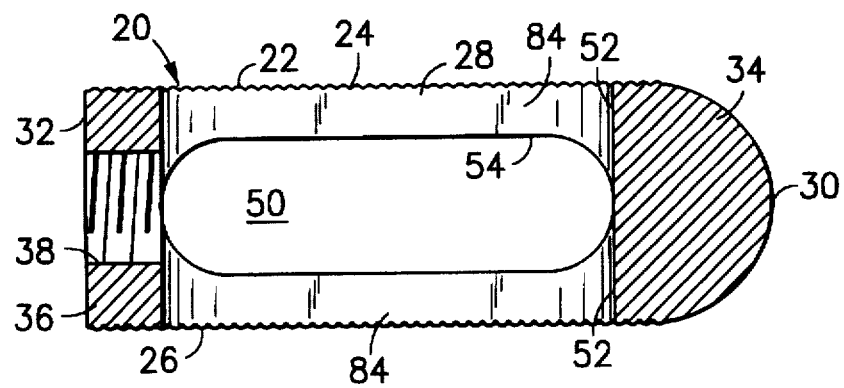
FIG. 6 is an enlarged longitudinal cross-sectional view of the prosthetic implant, taken along line 6—6 of FIG. 2.

Referring to FIGS. 2 and 3, the tip 34 has a surface contour configuration which is tapered from transverse cross-sectional profiles of lesser height and narrower width adjacent the front end 30 toward transverse cross-sectional profiles of greater height and wider width adjacent the upper and lower surfaces 24 and 26. In the preferred construction, the surface contour configuration of tip 34 is ogival in at least horizontal planes, and preferably is ogival in both horizontal and vertical planes. As best seen in FIG. 6, a chamber 50 extends longitudinally within the rigid member 22, between the tip 34 and the rear wall 36. Oblong openings 52 at the upper and lower surfaces 24 and 26 communicate with the chamber 50, the oblong openings 52 each having a generally trapezoidal configuration (see FIG. 2). Likewise, further oblong openings 54 at the sides 28 communicate with the chamber 50, the further oblong openings 54 having a generally oval configuration, all for purposes which will be made apparent hereinafter.

Figure 7:
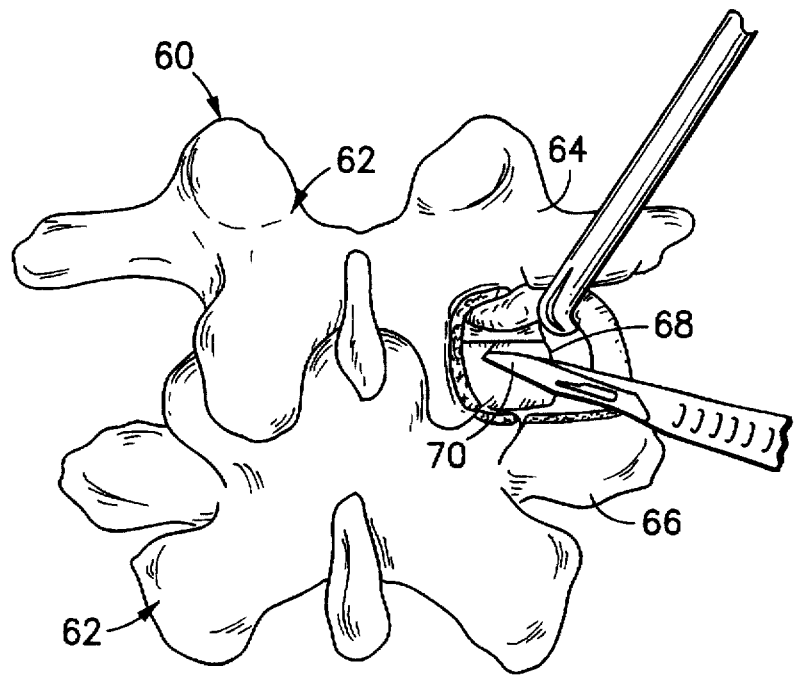
FIGS. 7 through 14 are somewhat diagrammatic pictorial views illustrating an implant procedure by which the prosthetic implant is placed between vertebral bodies in a spine.
Figure 8:
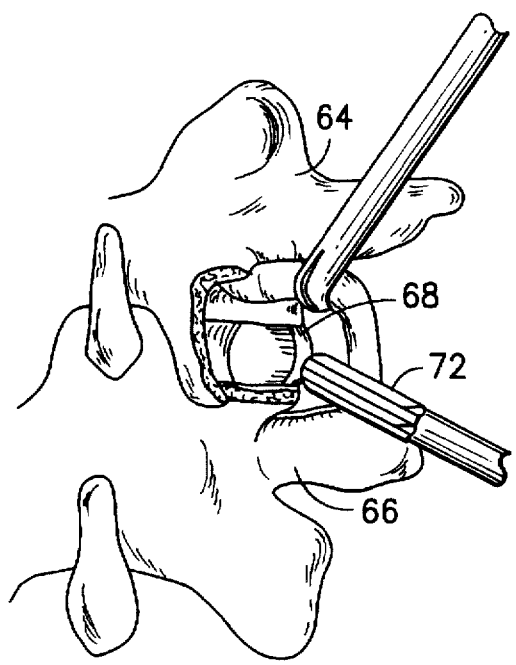
Figure 9:
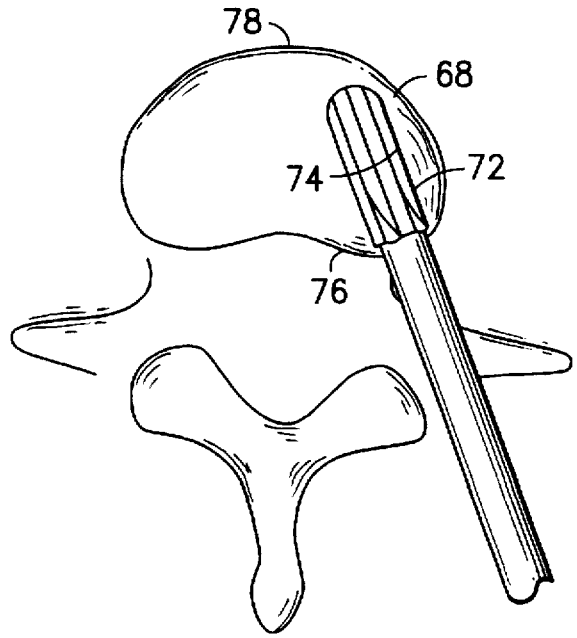
Figure 10:
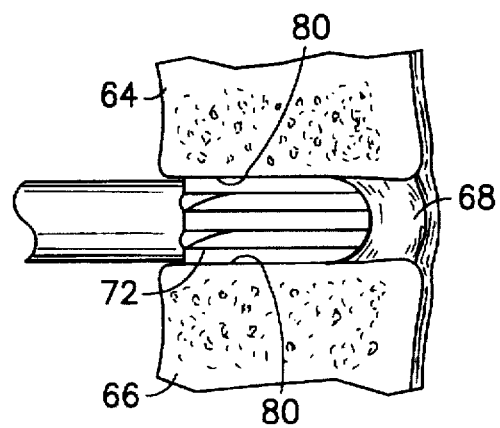

Turning now to FIGS. 7 through 14, prosthetic implant 20 is to be placed between adjacent vertebral bodies of the vertebrae of a spine and seated upon confronting end plates of the adjacent vertebral bodies to maintain a desired orientation and spacing between the adjacent vertebral bodies and support the adjacent vertebral bodies for fusion at the desired orientation and spacing, in the treatment of patients with ruptured or otherwise degenerated intervertebral discs. Thus, as seen in FIG. 7, a spine 60 having a plurality of vertebrae 62 includes adjacent vertebral bodies 64 and 66 between which there is a degenerated disc 68. Disc 68 has been approached from the posterior and has been exposed for excision by a scalpel 70 to excise a portion of the disc 68 for the reception of a reamer 72, as shown in FIG. 8. Reamer 72 is of a size selected to match the desired spacing between the adjacent vertebral bodies 64 and 66 and is driven into the disc 68 until the reamer 72 is fully within the disc 68, as shown in the diagrammatic anterior/posterior illustration of FIG. 9 and the diagrammatic sagittal illustration of FIG. 10. The diameter of the reamer 72, as determined by the selected size of the reamer 72, matches the desired spacing and creates a bore 74 in the tissue of the disc 68, the bore 74 extending from the posterior 76 toward the anterior 78 of the disc 68. At the same time, the diameter of the reamer 72 allows the reamer 72 to contact the confronting end plates 80 of the adjacent vertebral bodies 64 and 66, and the hard bone of the end plates 80 is prepared for the reception of the prosthetic implant 20, without cutting into the bone itself.

Figure 11:
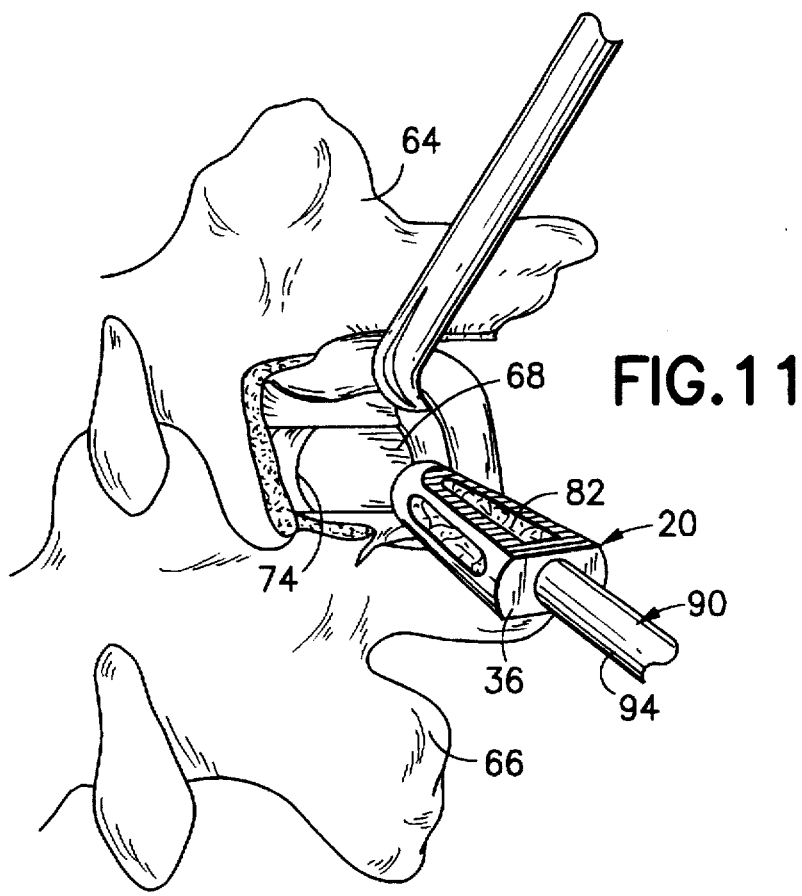
Figure 12:
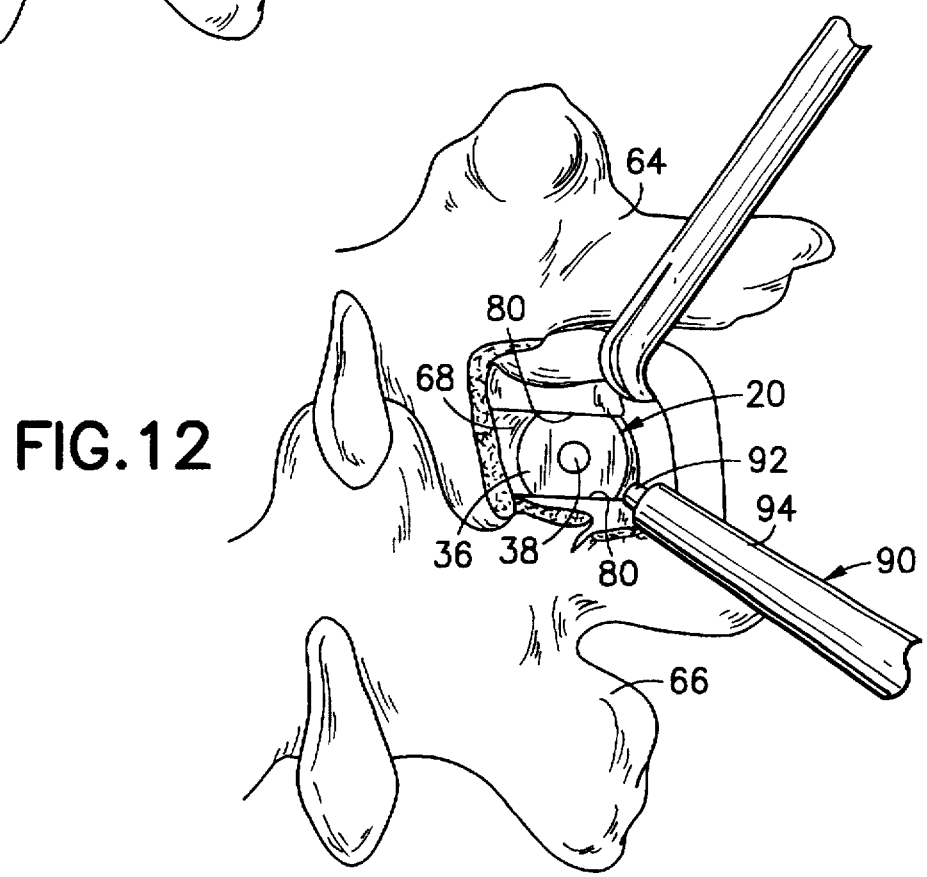
Figure 13:
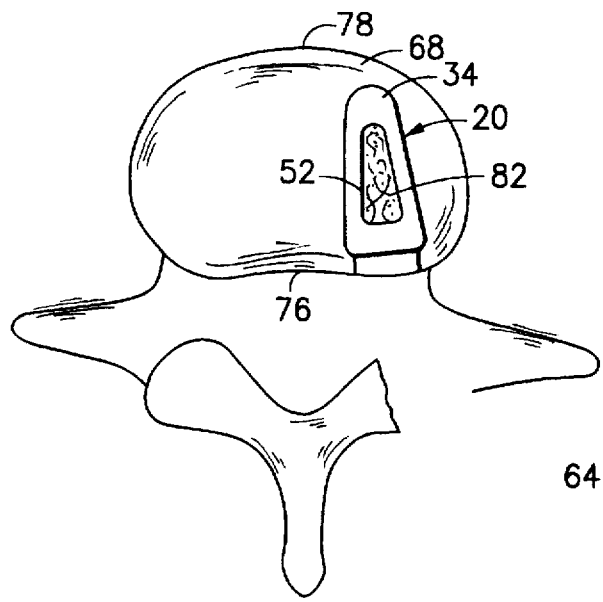
Figure 14:
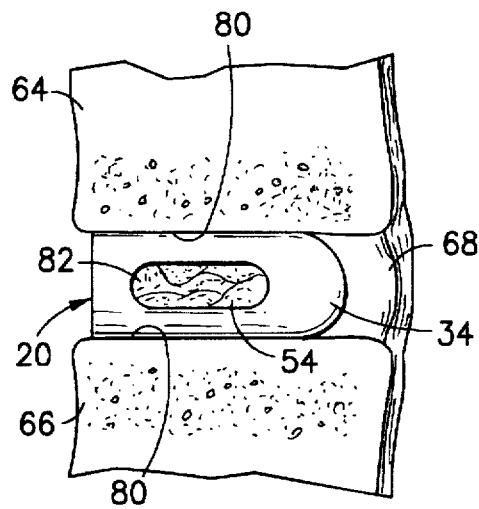

Turning now to FIG. 11, the prosthetic implant 20 has been coupled with an insertion instrument 90 by means of a threaded stud 92 (see FIG. 12) which projects axially from handle 94 of the instrument 90 to engage threaded hole 38 in the rear wall 36 of the rigid member 22. The prosthetic implant 20 then is placed between the prepared end plates 80 by advancing the instrument 90, with the attached prosthetic implant 20, in the posterior to anterior direction, inserting the prosthetic implant 20 into the bore 74 of the prepared disc 68, and advancing the prosthetic implant 20 until the prosthetic implant 20 is seated appropriately between the confronting end plates 80 of the vertebral bodies 64 and 66. The instrument 90 then is uncoupled from the prosthetic implant 20, as shown in the posterior diagrammatic view of FIG. 12, leaving the prosthetic implant 20 placed between the adjacent vertebral bodies 64 and 66, as seen in the diagrammatic anterior/posterior view of FIG. 13 and the diagrammatic sagittal view of FIG. 14.

The wedge-shaped configuration of the rigid member 22, with the width W greater than the height H, and thus greater than the diameter of the bore 74, facilitates insertion of the prosthetic implant 20 into the bore 74 of the prepared disc 68 and capture of the prosthetic implant 20 by wedging of the rigid member 22 within the resilient tissue of the disc 68 to secure the prosthetic implant 20 in the appropriate desired location between the adjacent vertebral bodies 64 and 66, as shown. At the same time, the wedge-shaped configuration provides a greater area along upper and lower surfaces 24 and 26 for enhanced load distribution and concomitant reduced risk of impaction of the bone at the end plates 80. To this end, angle A preferably is in the range of about 40° to about 80°.

The ogival surface contour of the tip 34 of the rigid member 22 further facilitates the introduction, reception and insertion of the prosthetic implant 20 within the bore 74 of disc 68, while at the same time reducing the risk of contusion of neurological elements in the vicinity during the implant procedure in that these neurological elements merely are deflected by the ogival shape of tip 34, without injury, during implantation. The contour of the upper and lower surfaces 24 and 26 assure firm seating of the rigid member 22 upon the confronting end plates 80 of the adjacent vertebral bodies 64 and 66, and the serrations 40 on the upper and lower surfaces 24 and 26 assure that upon seating of the surfaces 24 and 26 against the corresponding end plates 80, the surfaces 24 and 26 engage and grip the end plates 80 to secure the prosthetic implant 20 in place so as to maintain the desired orientation and spacing between the adjacent vertebral bodies 64 and 66 and promote fusion of the vertebral bodies 64 and 66 at the desired orientation and spacing.

Fusion is promoted further by filling the chamber 50 with bone graft material 82 prior to insertion of the prosthetic implant 20. The preferred bone graft material 82 is morselized bone, either autologous or homologous, or bone graft substitutes, and fills the chamber 50 so that the bone graft material 82 will be exposed directly to the end plates 80 through the openings 52. The extent and configuration of the openings 52 establish areas of contact which assure maximum contact between the bone graft material 82 in the chamber 50 and the adjacent vertebral bodies 64 and 66, while maintaining compressive strength in the rigid member 22 so that fusion is promoted while the vertebral bodies 64 and 66 are maintained at the desired orientation and spacing. At the same time, the openings 54 at the sides 28 of the rigid member 22 facilitate the circulation of blood to the bone graft material 82 to accelerate fusion.

It is noted that the placement of the chamber 50 relative to the tip 34 and the rear wall 36 enables the tip 34 and the rear wall 36 both to be constructed of solid material for greater strength, enabling the rigid member 22 to withstand the forces applied during insertion of the prosthetic implant 20, as described above, as well as compressive forces encountered subsequently, during fusion. The overall construction of the rigid member 22 is a cage-like structure in which the solid tip 34 and the rear wall 36 are connected by longitudinal struts 84 for a rigid, sturdy yet open structure enabling reception of the bone graft material 82. The rigid member 22 preferably is constructed of a rugged biocompatible material, the preferred material being a titanium alloy selected from a variety of such alloys currently available for biomechanical uses. Such an alloy has the further advantage of being suitable for visualization by either radiological or magnetic resonance imaging (MRI) techniques.

Referring now to FIGS. 15 and 16, another prosthetic implant constructed in accordance with the invention is illustrated at 120 and is seen to have a construction similar to that of the embodiment described above in connection with FIGS. 1 through 16, in that a wedge-shaped rigid member 122, tapered at an angle A, includes a superior or upper load-bearing surface 124 and an inferior or lower load-bearing surface 126, an ogival tip 130 connected to a rear wall 132 by longitudinal struts 134, and a chamber 135 located between the tip 130 and the rear wall 132. In the present embodiment, however, the rigid member 122 includes a maximum width WW located intermediate the front end 136 and the rear end 138 of the rigid member 122, and a further wedge-shaped configuration tapers along a posterior or rearward portion 140 of the rigid member 122, at an angle B, from narrower widths adjacent the rear end 138 to wider widths adjacent the maximum width WW. This posteriorly or rearwardly tapered portion 140 enables the tissue of the disc within which the prosthetic implant 120 is inserted to tend to close around the rearward portion 140 of the rigid member 122, subsequent to implantation, thereby enhancing the securement of the prosthetic implant 120 within the disc upon completion of the implantation. In the preferred construction, the maximum width WW is located longitudinally so as to be spaced from the front end 136 about three-quarters of the length of the rigid member 122 between the front end 136 and the rear end 138, and the angle B is about 40°.

Figure 15:
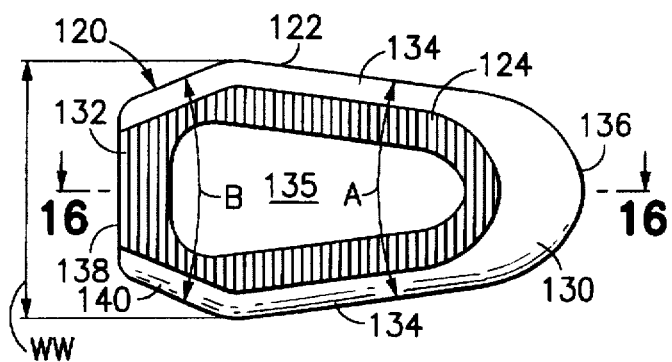
FIG. 15 is a top plan view of another prosthetic implant constructed in accordance with the present invention.
Figure 16:
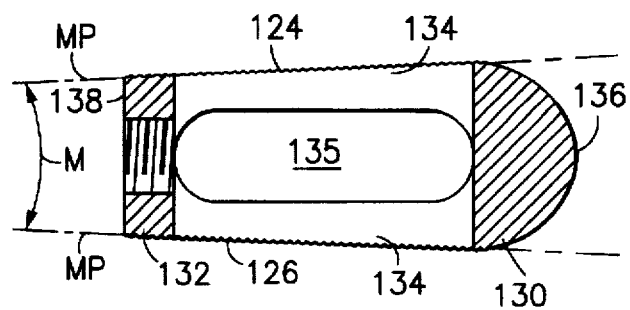
FIG. 16 is a longitudinal cross-sectional view taken along line 16—16 of FIG. 15.

Also illustrated in connection with the embodiment of FIGS. 15 and 16 is the placement of the upper and lower surfaces 124 and 126 in mean planes MP oriented at an angle M to one another such that the altitudinal distance between the upper and lower surfaces 124 and 126 varies from a greater height at the front end 136 of the rigid member 122 to a lesser height at the rear end 138. The choice of angle M is dependent upon where in the spinal column the prosthetic implant is to be inserted. Thus, in superior or upper lumbar locations the confronting end plates of adjacent vertebrae essentially are parallel, and that parallel relationship is to be preserved and maintained by employing a prosthetic implant 120 in which the upper and lower load-bearing surfaces 124 and 126 (or upper and lower surfaces 24 and 26 in prosthetic implant 20) follow essentially parallel mean planes MP. However, in inferior or lower lumbar locations, and in adjacent sacral locations, the confronting end plates of adjacent vertebrae are not parallel, but converge somewhat in the posterior direction. In order to preserve and maintain the converging relationship upon implanting a prosthetic implant, the mean planes MP are placed at angle M, with the upper and lower surfaces 124 and 126 (or upper and lower surfaces 24 and 26) following the converging relationship. The preferred range of angle M, in order to accommodate the convergence encountered between the end plates of adjacent vertebral bodies between which a prosthetic implant is to be placed, is up to about 8°.

It will be seen that the present invention attains the several objects and advantages summarized above, namely: Restores intervertebral orientation and spacing between adjacent vertebral bodies, in the treatment of ruptured, herniated, or otherwise degenerated intervertebral discs, or indications of spondylothesis, and enables fusion between the adjacent vertebral bodies, with less invasive surgical procedures; provides a construction and configuration which facilitates appropriate introduction and placement of the prosthesis during implant, while reducing the risk of injury to surrounding tissue and organs; enables improved load distribution for reducing the risk of impaction of the bone of the surrounding vertebral bodies between which the prosthesis is placed; provides for relatively high strength support between adjacent vertebral bodies during fusion while placing graft material in position for maximum contact between the graft material and the adjacent vertebral bodies so as to promote and accelerate fusion; facilitates visualization of the placement of the prosthetic implant through the use of conventional radiological and magnetic resonance imaging (MRI) techniques; enables relatively economical manufacture with consistent high quality.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An interbody spinal prosthetic implant for placement between adjacent vertebral bodies of the vertebrae of a spine and seating upon confronting end plates of the adjacent vertebral bodies to maintain a desired orientation and a desired spacing between the adjacent vertebral bodies and support the adjacent vertebral bodies for fusion at the desired orientation and the desired spacing, the prosthetic implant comprising:

- a rigid member of biocompatible material having vertically opposite upper and lower load-bearing surfaces spaced apart altitudinally to define a height and located along mean planes extending in generally longitudinal directions corresponding to the desired orientation, the load-bearing surfaces being spaced apart a distance corresponding to the desired spacing, the rigid member including,
- a front end, a rear end spaced longitudinally from the front end to define a length, and sides spaced apart laterally to define a width, said sides extending generally longitudinally at an angle to one another to define a wedge-shaped configuration in the rigid member in horizontal planes, the wedge-shaped configuration tapering from narrower widths adjacent the front end toward wider widths adjacent the rear end and including an overall width greater than the height between the upper and lower load-bearing surfaces; and
- a tip extending longitudinally between the front end and the load-bearing surfaces, the tip having a surface contour configuration tapered from transverse cross-sectional profiles of relatively lesser height and relatively narrower width adjacent the front end toward transverse cross-sectional profiles of relatively greater height and relatively wider width adjacent the load-bearing surfaces such that the surface contour configuration of the tip follows an ogival profile including a continuous curve from the front end to the load-bearing surfaces and from the front end to the sides of the rigid member.

2. The invention of claim 1 wherein the sides each have a convex arcuate surface contour configuration, in lateral planes, extending altitudinally between the upper and lower load-bearing surfaces.

3. The invention of claim 2 wherein the rigid member has a central longitudinal axis and the convex arcuate surface contour configuration of each side lies on a circle centered on the central longitudinal axis and having a diameter greater than the height of the rigid member.

4. The invention of claim 2 wherein the angle between the sides is about 4° to about 8°.

5. The invention of claim 1 wherein the angle between the sides is about 4° to about 8°.

6. The invention of claim 1 wherein the mean planes are parallel to one another.

7. The invention of claim 1 wherein the mean planes are oriented at an angle to one another such that the distance between the upper and lower load-bearing surfaces varies from a greater height adjacent the front end to a lesser height adjacent the rear end.

8. The invention of claim 7 wherein the angle between the upper and lower load-bearing surfaces is up to about 8°.

9. The invention of claim 1 wherein the rigid member includes a maximum width intermediate the front end and the rear end, and the sides extend generally longitudinally at a further angle to one another along a further wedge-shaped configuration in horizontal planes, the further wedge-shaped configuration tapering from relatively narrower widths adjacent the rear end toward relatively wider widths adjacent the maximum width.

10. The invention of claim 9 wherein the further angle is about 40°.

11. The invention of claim 9 wherein the maximum width is spaced from the front end about three-quarters of the length of the rigid member.

12. The invention of claim 1 wherein the rigid member includes a chamber within the rigid member for containing bone graft material, and oblong openings at the upper and lower load-bearing surfaces, the oblong openings communicating with the chamber for establishing areas of contact between the end plates and the bone graft material subsequent to placement of the prosthetic implant between the adjacent vertebral bodies.

13. The invention of claim 12 wherein the chamber is spaced rearwardly from the front end so that the tip is solid.

14. The invention of claim 12 including further oblong openings in the sides of the rigid member, the further oblong openings communicating with the chamber for further facilitating the circulation of blood to the bone graft material in the chamber.

15. The invention of claim 1 wherein the upper and lower load-bearing surfaces include laterally oriented serrations for enhancing securement of the rigid member between the adjacent vertebral bodies subsequent to placement of the rigid member between the vertebral bodies.

16. The invention of claim 1 wherein the biocompatible material is a titanium alloy.

17. The invention of claim 1 wherein the rigid member includes a rear wall at the rear end.

18. The invention of claim 17 including a threaded hole in the rear wall, the threaded hole extending longitudinally from the rear end toward the front end.

19. The invention of claim 17 wherein the rigid member comprises a unitary construction including the tip and the rear wall.

20. The invention of claim 19 wherein the biocompatible material is a titanium alloy.

* * * * *